US010781423B2

(12) United States Patent
Kitamura et al.

(10) Patent No.: US 10,781,423 B2
(45) Date of Patent: Sep. 22, 2020

(54) METHOD FOR PRODUCING B CELL POPULATION

(71) Applicants: TOKYO UNIVERSITY OF SCIENCE FOUNDATION, Tokyo (JP); KANEKA CORPORATION, Osaka-shi, Osaka (JP)

(72) Inventors: Daisuke Kitamura, Tokyo (JP); Tomoyuki Nakaishi, Takasago (JP)

(73) Assignees: TOKYO UNIVERSITY OF SCIENCE FOUNDATION, Tokyo (JP); KANEKA CORPORATION, Osaka-Shi (JP)

( * ) Notice: Subject to any disclaimer, the term of this patent is extended or adjusted under 35 U.S.C. 154(b) by 193 days.

(21) Appl. No.: 16/180,592

(22) Filed: Nov. 5, 2018

(65) Prior Publication Data

US 2020/0255802 A1 Aug. 13, 2020

Related U.S. Application Data

(62) Division of application No. 15/322,325, filed as application No. PCT/JP2015/068789 on Jun. 30, 2015, now Pat. No. 10,428,304.

(30) Foreign Application Priority Data

Jul. 2, 2014 (JP) .................................. 2014-136631

(51) Int. Cl.
| | | |
|---|---|---|
| *C12N 5/00* | (2006.01) | |
| *C12N 5/02* | (2006.01) | |
| *A61K 38/00* | (2006.01) | |
| *C12N 5/0781* | (2010.01) | |
| *C12N 15/09* | (2006.01) | |
| *C12N 5/10* | (2006.01) | |
| *C12N 15/86* | (2006.01) | |
| *C07K 16/00* | (2006.01) | |
| *C07K 14/47* | (2006.01) | |
| *C12N 7/00* | (2006.01) | |

(52) U.S. Cl.
CPC ........ *C12N 5/0635* (2013.01); *C07K 14/4702* (2013.01); *C07K 16/00* (2013.01); *C12N 5/10* (2013.01); *C12N 7/00* (2013.01); *C12N 15/09* (2013.01); *C12N 15/86* (2013.01); *C07K 2317/14* (2013.01); *C12N 2740/15043* (2013.01)

(58) Field of Classification Search
None
See application file for complete search history.

(56) References Cited

FOREIGN PATENT DOCUMENTS

| JP | 9-512441 A1 | 12/1997 |
|---|---|---|
| JP | 2009-142292 A | 7/2009 |
| JP | 2011-092142 A | 5/2011 |
| JP | 2013-99358 A | 5/2013 |
| WO | WO 95/29935 A1 | 11/1995 |
| WO | WO 2005/110433 A1 | 11/2005 |
| WO | WO 2011/052545 A1 | 5/2011 |

OTHER PUBLICATIONS

Atsushi Ono et al; Nuclear Positioning of the BACH2 Gene . . . ; Genes, Chromosomes & Cancer, 2007, vol. 46; pp. 67-74.
Jukka Alinikula et al.; Alternate pathways for Bcl6-mediated regulation of B cell to plasma . . . ; Eur. J. Immunol; 2011; vol. 41; pp. 2404-2413.
Miki Watanabe-Matsui et al.; Heme regulates B-cell differentiation, antibody class switch . . . ; Blood, 2011; vol. 117; pp. 5438-5448.
Non-Final Office Action dated Jan. 4, 2019 in parent U.S. Appl. No. 15/322,325.
European Office Action, dated Nov. 26, 2018, for corresponding European Application No. 15814202.6.
Extended European Search Report, dated Oct. 26, 2017, for corresponding European Application No. 15814202.6.
International Preliminary Report on Patentability issued in PCT/JP2015/068789, dated Jan. 12, 2017 (Forms PCT/IB/326/PCT/IB/373 and PCT/ISA/237).
International Search Report issued in PCT/JP2015/078789, dated Sep. 15, 2015 (Forms PCT/ISA/220, PCT/ISA/210 and PCT/ISA/237).
Kikuchi et al., "Over-expression of BACH2 is related to ongoing somatic hypermutation of the immunoglobulin heavy chain gene variable region of de novo diffuse large B-cell lymphoma," Pathology international, vol. 63, No. 7, Jul. 2013, pp. 339-344.
Melanie K. Spriggs et al.; Recombinant Human CD40 Ligand Stimulates . . . ; J. Exp. Med. Dec. 1992; vol. 176(6); pp. 1543-1550.
Mizuho Morooka et al.; The essential role of Bach2 in B-cell receptor-induced proliferation . . . ; Proceedings for the Japanese Society for Immunology; Nov. 18, 2013; vol. 42; No. proceeding; pp. 161 (2-H-W38-12-P).
Nojima et al., "In-vitro derived germinal centre B cells differentially generate memory B or plasma cells in vivo," Nature Communications, vol. 2, No. 465, Sep. 6, 2011, pp. 1-11.
Ochiai et al., "Plasmacytic transcription factor Blimp-1 is repressed by Bach2 in B cells," Journal of Biological Chemistry, vol. 281, No. 50, Dec. 15, 2006 (published online Oct. 17, 2006), pp. 38226-38234 (10 pages total).

(Continued)

*Primary Examiner* — Michail A Belyavskyi
(74) *Attorney, Agent, or Firm* — Birch, Stewart, Kolasch & Birch, LLP

(57) ABSTRACT

It is an object of the present invention to provide a method for easily producing an antigen-specific B cell population comprising IgG-positive B cells specific to a specific antigen. The present invention provides a method for producing a B cell population, comprising culturing B cells, in which the expression of a Bach2 gene has been increased, in the presence of a means for acting on CD40 and/or a BAFF receptor.

1 Claim, 3 Drawing Sheets

Specification includes a Sequence Listing.

(56) References Cited

OTHER PUBLICATIONS

Shinya Sasaki et al.; Cloning and expresssion of human B cell-specific transcription . . . ; Oncogene; 2000; No. 19; pp. 3739-3749.
Takuya Nojima et al.; Toward the establishment of general center-like B cell culture system; Abstracts of the Annual Meetings of the Japanese Society for Immunology, 2007; vol. 37; p. 259; 3-F-W41-16-O/P.
Y. Miura et al.; Transcriptional repressor Bach 2 promotes B cell . . . ; Annual Meeting of the Molecular Biology Society of Japan Program Yoshishu(Web); 2011; vol. 34; pp. 4P-0422 (Web Only).
Office Action dated Aug. 15, 2018 in parent U.S. Appl. No. 15/322,325.
Japanese Notice of Reasons for Refusal for corresponding Japanese Application No, 2016-531384, dated Apr. 2, 2019, with English translation.

[Figure 1]
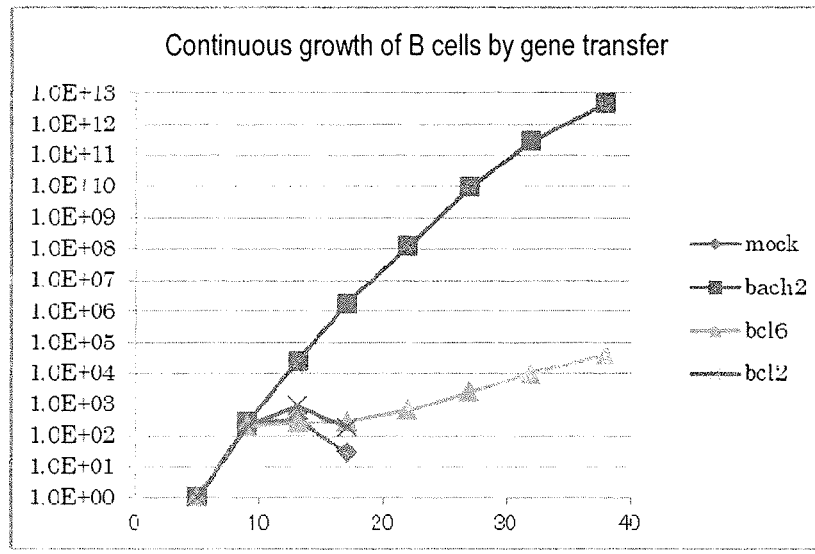
[Figure 2]
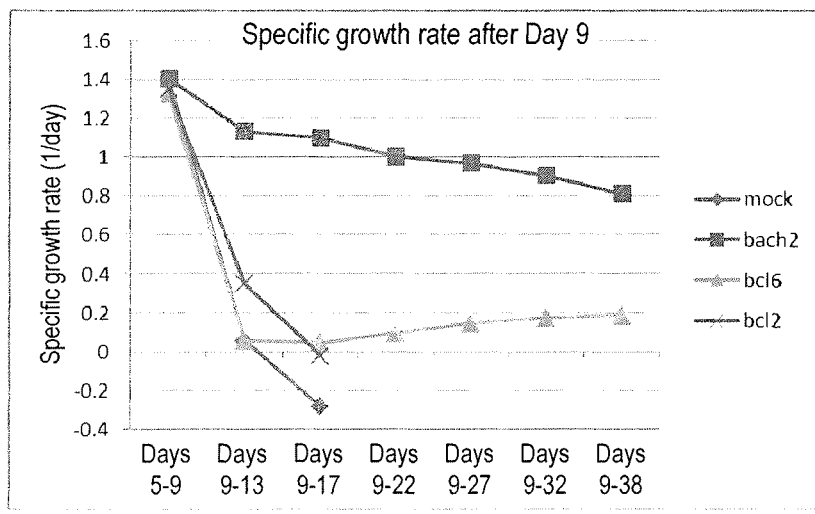

[Figure 3]
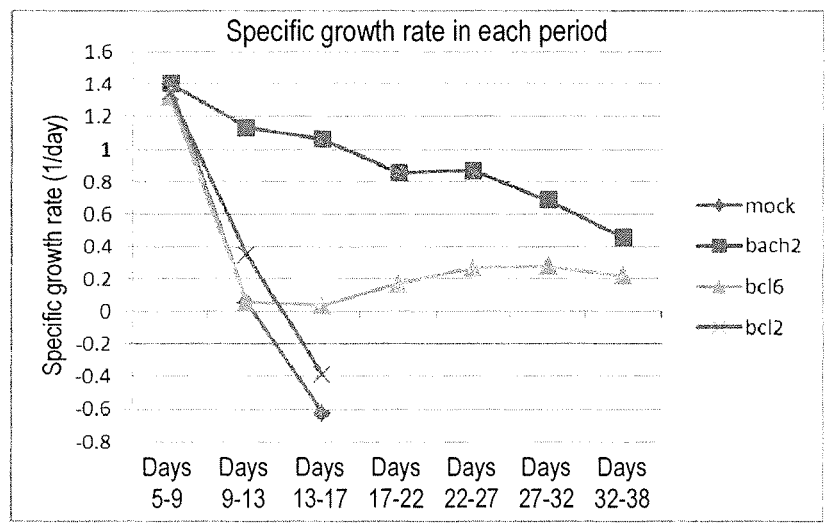
[Figure 4]
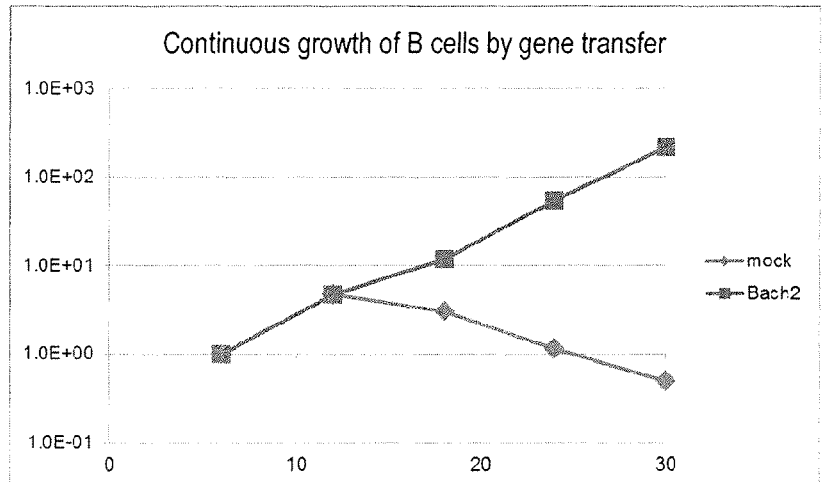

[Figure 5]
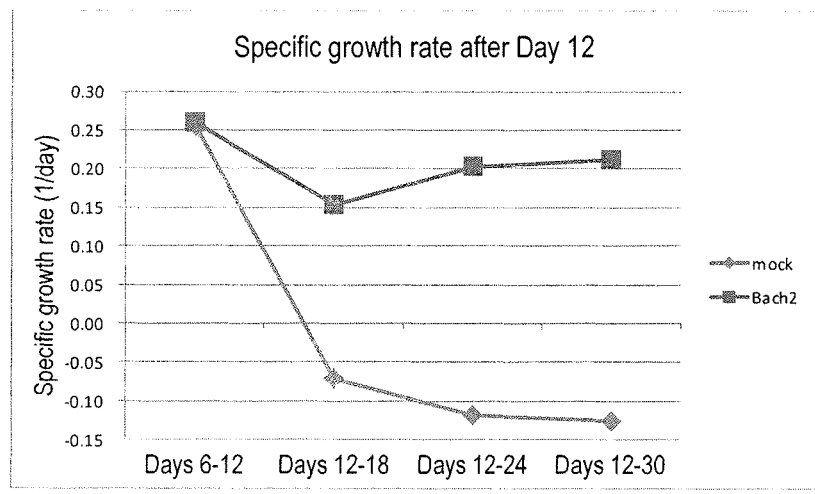
[Figure 6]
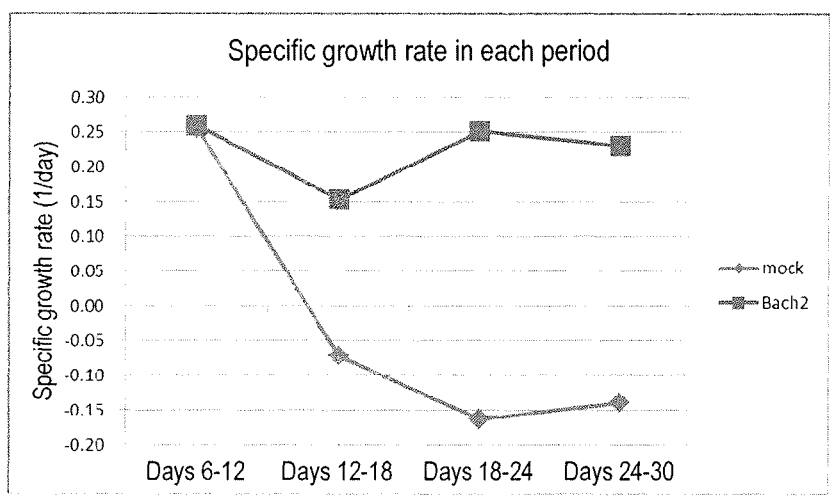

SEQUENCE LISTING

<160> NUMBER OF SEQ ID NOS: 2

<210> SEQ ID NO 1
<211> LENGTH: 839
<212> TYPE: PRT
<213> ORGANISM: mouse

<400> SEQUENCE: 1

```
Met Ser Val Asp Glu Lys Pro Gly Ser Pro Met Tyr Val Tyr Glu Ser
1               5                   10                  15

Thr Val His Cys Ala Asn Ile Leu Leu Gly Leu Asn Asp Gln Arg Lys
            20                  25                  30

Lys Asp Ile Leu Cys Asp Val Thr Leu Ile Val Glu Arg Lys Glu Phe
        35                  40                  45

Arg Ala His Arg Ala Val Leu Ala Ala Cys Ser Glu Tyr Phe Trp Gln
    50                  55                  60

Ala Leu Val Gly Gln Thr Lys Asp Asp Leu Val Val Ser Leu Pro Glu
65                  70                  75                  80

Glu Val Thr Ala Arg Gly Phe Gly Pro Leu Leu Gln Phe Ala Tyr Thr
                85                  90                  95

Ala Lys Leu Leu Leu Ser Arg Glu Asn Ile Arg Glu Val Ile Arg Cys
            100                 105                 110

Ala Glu Phe Leu Arg Met His Asn Leu Glu Asp Ser Cys Phe Ser Phe
        115                 120                 125

Leu Gln Thr Gln Leu Leu Asn Arg Glu Asp Gly Leu Phe Val Cys Arg
    130                 135                 140

Lys Asp Ser Ala Cys Gln Arg Pro Gln Glu Asp His Gly Asn Ser Ala
145                 150                 155                 160

Gly Glu Glu Glu Glu Glu Glu Thr Met Asp Ser Glu Thr Ala Arg
                165                 170                 175

Met Ala Cys Ala Thr Asp Gln Met Leu Pro Asp Pro Ile Ser Phe Glu
            180                 185                 190

Ala Thr Ala Ile Pro Val Ala Glu Lys Glu Glu Ala Leu Leu Pro Glu
        195                 200                 205

Ser Glu Val Pro Thr Asp Thr Lys Glu Asn Ser Glu Lys Gly Ala Leu
    210                 215                 220
```

```
Thr Gln Tyr Pro Arg Tyr Lys Lys Tyr Gln Leu Ala Cys Thr Lys Asn
225                 230                 235                 240

Val Tyr Ser Ala Pro Ser His Gly Thr Ser Gly Phe Ala Ser Thr Phe
            245                 250                 255

Ser Glu Asp Ser Pro Gly Asn Ser Leu Lys Pro Gly Leu Pro Met Gly
        260                 265                 270

Gln Ile Lys Ser Glu Pro Pro Ser Glu Glu Thr Glu Glu Glu Ser Ile
                275                 280                 285

Thr Leu Cys Leu Ser Gly Asp Glu Thr Asp Ile Lys Asp Arg Pro Gly
290                 295                 300

Asp Val Glu Met Asp Arg Lys Gln Pro Ser Pro Ala Pro Thr Pro Ser
305                 310                 315                 320

Thr Pro Thr Gly Ala Ala Cys Leu Asp Arg Ser Arg Ser Val Ser Ser
            325                 330                 335

Pro Ser Cys Leu Arg Ser Leu Phe Gly Ile Thr Lys Gly Val Glu Ser
        340                 345                 350

Thr Gly Leu Pro Ser Thr Ser Gln Gln Pro Leu Val Arg Ser Ser Ala
            355                 360                 365

Cys Pro Phe Asn Lys Gly Ile Ser Gln Gly Asp Leu Lys Thr Asp Tyr
370                 375                 380

Thr Pro Leu Ala Gly Asn Tyr Gly Gln Pro His Val Gly Gln Lys Asp
385                 390                 395                 400

Val Ser Asn Phe Ala Met Gly Ser Pro Leu Arg Gly Pro Gly Pro Glu
                405                 410                 415

Thr Leu Cys Lys Gln Glu Gly Glu Leu Asp Arg Arg Ser Val Ile Phe
            420                 425                 430

Ser Ala Ser Ala Cys Asp Gln Pro Asn Thr Pro Val His Ser Tyr Ser
        435                 440                 445

Ala Val Ser Asn Leu Asp Lys Asp Leu Ser Glu Pro Val Pro Lys Ser
    450                 455                 460

Leu Trp Val Gly Ala Gly Gln Ser Leu Pro Ser Ser Gln Ala Tyr Ser
465                 470                 475                 480

His Ser Gly Leu Met Ala Asp His Leu Pro Gly Arg Ile Arg Pro Asn
                485                 490                 495

Thr Ser Cys Pro Val Pro Ile Lys Val Cys Pro Arg Ser Pro Pro Leu
            500                 505                 510

Glu Thr Arg Thr Arg Thr Ser Ser Ser Cys Ser Ser Tyr Ser Tyr Ala
        515                 520                 525

Glu Asp Gly Ser Gly Gly Ser Pro Cys Ser Leu Pro Leu Cys Glu Phe
    530                 535                 540

Ser Ser Ser Pro Cys Ser Gln Gly Ala Arg Phe Leu Ala Thr Glu His
545                 550                 555                 560

Gln Glu Pro Gly Leu Met Gly Asp Gly Met Tyr Asn Gln Val Arg Pro
                565                 570                 575

Gln Ile Lys Cys Glu Gln Ser Tyr Gly Thr Asn Ser Ser Asp Glu Ser
            580                 585                 590

Gly Ser Phe Ser Glu Ala Asp Ser Glu Ser Cys Pro Val Gln Asp Arg
        595                 600                 605

Gly Gln Glu Val Lys Leu Pro Phe Pro Val Asp Gln Ile Thr Asp Leu
    610                 615                 620

Pro Arg Asn Asp Phe Gln Met Met Ile Lys Met His Lys Leu Thr Ser
625                 630                 635                 640

Glu Gln Leu Glu Phe Ile His Asp Ile Arg Arg Arg Ser Lys Asn Arg
```

```
              645                 650                 655
Ile Ala Ala Gln Arg Cys Arg Lys Arg Lys Leu Asp Cys Ile Gln Asn
            660                 665                 670

Leu Glu Cys Glu Ile Arg Lys Leu Val Cys Glu Lys Glu Lys Leu Leu
            675                 680                 685

Ser Glu Arg Asn His Leu Lys Ala Cys Met Gly Leu Leu Asp Asn
            690                 695                 700

Phe Ser Cys Leu Ser Gln Glu Val Cys Arg Asp Ile Gln Ser Pro Glu
705                 710                 715                 720

Gln Ile Gln Ala Leu His Arg Tyr Cys Pro Val Leu Ile Pro Met Asp
                725                 730                 735

Leu Pro Gly Ala Ser Val Asn Pro Pro Val Gly Val Glu Gln Ser
            740                 745                 750

Leu Ala Pro Ser Pro Cys Ala Val Gly Gly Ser Val Pro Cys Cys Leu
            755                 760                 765

Glu Pro Gly Ala Ala Pro Pro Gly Leu Pro Trp Val Pro Ser Asn Thr
            770                 775                 780

Ser Glu Asn Cys Thr Ser Gly Arg Arg Leu Glu Gly Ser Asp Pro Gly
785                 790                 795                 800

Thr Phe Ser Glu Arg Gly Pro Pro Leu Glu Ala Arg Ser Gln Ser Val
                805                 810                 815

Thr Val Asp Phe Cys Gln Glu Met Thr Glu Lys Cys Thr Thr Asp Glu
                820                 825                 830

Gln Pro Arg Lys Asp Tyr Ala
            835

<210> SEQ ID NO 2
<211> LENGTH: 841
<212> TYPE: PRT
<213> ORGANISM: human

<400> SEQUENCE: 2

Met Ser Val Asp Glu Lys Pro Asp Ser Pro Met Tyr Val Tyr Glu Ser
1               5                   10                  15

Thr Val His Cys Thr Asn Ile Leu Leu Gly Leu Asn Asp Gln Arg Lys
                20                  25                  30

Lys Asp Ile Leu Cys Asp Val Thr Leu Ile Val Glu Arg Lys Glu Phe
            35                  40                  45

Arg Ala His Arg Ala Val Leu Ala Ala Cys Ser Glu Tyr Phe Trp Gln
    50                  55                  60

Ala Leu Val Gly Gln Thr Lys Asn Asp Leu Val Val Ser Leu Pro Glu
65                  70                  75                  80

Glu Val Thr Ala Arg Gly Phe Gly Pro Leu Leu Gln Phe Ala Tyr Thr
                85                  90                  95

Ala Lys Leu Leu Leu Ser Arg Glu Asn Ile Arg Glu Val Ile Arg Cys
                100                 105                 110

Ala Glu Phe Leu Arg Met His Asn Leu Glu Asp Ser Cys Phe Ser Phe
            115                 120                 125

Leu Gln Thr Gln Leu Leu Asn Ser Glu Asp Gly Leu Phe Val Cys Arg
    130                 135                 140

Lys Asp Ala Ala Cys Gln Arg Pro His Glu Asp Cys Glu Asn Ser Ala
145                 150                 155                 160

Gly Glu Glu Glu Asp Glu Glu Glu Thr Met Asp Ser Glu Thr Ala
                165                 170                 175
```

```
Lys Met Ala Cys Pro Arg Asp Gln Met Leu Pro Glu Pro Ile Ser Phe
            180                 185                 190

Glu Ala Ala Ala Ile Pro Val Ala Glu Lys Glu Ala Leu Leu Pro
        195                 200                 205

Glu Pro Asp Val Pro Thr Asp Thr Lys Glu Ser Ser Glu Lys Asp Ala
210                 215                 220

Leu Thr Gln Tyr Pro Arg Tyr Lys Lys Tyr Gln Leu Ala Cys Thr Lys
225                 230                 235                 240

Asn Val Tyr Asn Ala Ser Ser His Ser Thr Ser Gly Phe Ala Ser Thr
                245                 250                 255

Phe Arg Glu Asp Asn Ser Ser Asn Ser Leu Lys Pro Gly Leu Ala Arg
            260                 265                 270

Gly Gln Ile Lys Ser Glu Pro Pro Ser Glu Glu Asn Glu Glu Glu Ser
            275                 280                 285

Ile Thr Leu Cys Leu Ser Gly Asp Glu Pro Asp Ala Lys Asp Arg Ala
            290                 295                 300

Gly Asp Val Glu Met Asp Arg Lys Gln Pro Ser Pro Ala Pro Thr Pro
305                 310                 315                 320

Thr Ala Pro Ala Gly Ala Ala Cys Leu Glu Arg Ser Arg Ser Val Ala
                325                 330                 335

Ser Pro Ser Cys Leu Arg Ser Leu Phe Ser Ile Thr Lys Ser Val Glu
            340                 345                 350

Leu Ser Gly Leu Pro Ser Thr Ser Gln Gln His Phe Ala Arg Ser Pro
            355                 360                 365

Ala Cys Pro Phe Asp Lys Gly Ile Thr Gln Gly Asp Leu Lys Thr Asp
370                 375                 380

Tyr Thr Pro Phe Thr Gly Asn Tyr Gly Gln Pro His Val Gly Gln Lys
385                 390                 395                 400

Glu Val Ser Asn Phe Thr Met Gly Ser Pro Leu Arg Gly Pro Gly Leu
                405                 410                 415

Glu Ala Leu Cys Lys Gln Glu Gly Glu Leu Asp Arg Arg Ser Val Ile
            420                 425                 430

Phe Ser Ser Ser Ala Cys Asp Gln Val Ser Thr Ser Val His Ser Tyr
            435                 440                 445

Ser Gly Val Ser Ser Leu Asp Lys Asp Leu Ser Glu Pro Val Pro Lys
            450                 455                 460

Gly Leu Trp Val Gly Ala Gly Gln Ser Leu Pro Ser Ser Gln Ala Tyr
465                 470                 475                 480

Ser His Gly Gly Leu Met Ala Asp His Leu Pro Gly Arg Met Arg Pro
                485                 490                 495

Asn Thr Ser Cys Pro Val Pro Ile Lys Val Cys Pro Arg Ser Pro Pro
            500                 505                 510

Leu Glu Thr Arg Thr Arg Thr Ser Ser Ser Cys Ser Ser Tyr Ser Tyr
            515                 520                 525

Ala Glu Asp Gly Ser Gly Gly Ser Pro Cys Ser Leu Pro Leu Cys Glu
            530                 535                 540

Phe Ser Ser Ser Pro Cys Ser Gln Gly Ala Arg Phe Leu Ala Thr Glu
545                 550                 555                 560

His Gln Glu Pro Gly Leu Met Gly Asp Gly Met Tyr Asn Gln Val Arg
                565                 570                 575

Pro Gln Ile Lys Cys Glu Gln Ser Tyr Gly Thr Asn Ser Ser Asp Glu
            580                 585                 590

Ser Gly Ser Phe Ser Glu Ala Asp Ser Glu Ser Cys Pro Val Gln Asp
```

```
                    595                 600                 605
Arg Gly Gln Glu Val Lys Leu Pro Phe Pro Val Asp Gln Ile Thr Asp
        610                 615                 620

Leu Pro Arg Asn Asp Phe Gln Met Met Ile Lys Met His Lys Leu Thr
625                 630                 635                 640

Ser Glu Gln Leu Glu Phe Ile His Asp Val Arg Arg Ser Lys Asn
            645                 650                 655

Arg Ile Ala Ala Gln Arg Cys Arg Lys Arg Lys Leu Asp Cys Ile Gln
        660                 665                 670

Asn Leu Glu Cys Glu Ile Arg Lys Leu Val Cys Glu Lys Glu Lys Leu
            675                 680                 685

Leu Ser Glu Arg Asn Gln Leu Lys Ala Cys Met Gly Glu Leu Leu Asp
        690                 695                 700

Asn Phe Ser Cys Leu Ser Gln Glu Val Cys Arg Asp Ile Gln Ser Pro
705                 710                 715                 720

Glu Gln Ile Gln Ala Leu His Arg Tyr Cys Pro Val Leu Arg Pro Met
            725                 730                 735

Asp Leu Pro Thr Ala Ser Ser Ile Asn Pro Ala Pro Leu Gly Ala Glu
            740                 745                 750

Gln Asn Ile Ala Ala Ser Gln Cys Ala Val Gly Glu Asn Val Pro Cys
            755                 760                 765

Cys Leu Glu Pro Gly Ala Ala Pro Pro Gly Pro Trp Ala Pro Ser
        770                 775                 780

Asn Thr Ser Glu Asn Cys Thr Ser Gly Arg Arg Leu Glu Gly Thr Asp
785                 790                 795                 800

Pro Gly Thr Phe Ser Glu Arg Gly Pro Pro Leu Glu Pro Arg Ser Gln
                805                 810                 815

Thr Val Thr Val Asp Phe Cys Gln Glu Met Thr Asp Lys Cys Thr Thr
            820                 825                 830

Asp Glu Gln Pro Arg Lys Asp Tyr Thr
            835                 840
```

METHOD FOR PRODUCING B CELL POPULATION

This application is a Divisional of U.S. application Ser. No. 15/322,325, filed Dec. 27, 2016, which is the U.S. National Phase of PCT/JP2015/068789, filed Jun. 30, 2015, which claims priority under 35 U.S.C. 119(a) to Japanese Patent Application No. 2014-136631, filed Jul. 2, 2014, the contents of which are incorporated by reference, in their entirety, into the present application.

TECHNICAL FIELD

The present invention relates to a method for producing a B cell population, a B cell population produced by the aforementioned method for producing a B cell population, and a method for producing a monoclonal antibody by using the same.

BACKGROUND ART

It is anticipated that a monoclonal antibody exhibiting high selectivity to a specific antigen will be developed as an antibody drug, and in particular, the development of antibody drugs targeting cancer cells has progressed. In order to apply a medicament comprising a monoclonal antibody as an active ingredient to the treatment for humans, administration of a human antibody with a small amount of foreign antigen is most ideal from the viewpoint of the avoidance of rejection. Hence, a large number of chimeric antibodies and humanized antibodies are developed.

In general, chimeric antibodies or humanized antibodies used for the treatment of humans are produced by immunizing mice or other animals with antigens several times, then fusing cells in the spleen or lymph nodes with myeloma cells to form hybridomas, and then applying a recombination technique to mouse IgG antibodies produced from the hybridomas. However, it takes much time to use an individual animal such as a mouse or to select hybridomas that generate antibodies exhibiting a high affinity. Moreover, it is necessary to confirm the activity of an antibody obtained by a recombination technique. Thus, it takes time to produce an antibody of interest by the aforementioned method, and further, the effects of the produced antibody cannot be secured until it is administered to a human. Furthermore, when an immunogen exhibits toxicity to individual, immunization to an individual is difficult. Further, when a protein antigen that is highly preserved among animal species is used as an antigen, an antibody is hardly generated due to immunological tolerance.

B cells are immune cells that are derived from bone marrow, have B cell receptors (BCR) on the surface thereof, and produce antibodies. Such B cells are generated from hematopoietic stem cells, and the cells are differentiated into B cells through the stage of pro-B cells and pre-B cells. It has been known that the B cells producing antibodies exhibiting a high affinity for antigens are selected in a germinal center. However, this selection mechanism has not yet been elucidated. If such B cells producing antibodies exhibiting a high affinity for specific antigens were allowed to artificially proliferate and could be then concentrated, monoclonal antibodies exhibiting a high affinity for specific antigens could be produced in a shorter time than previous techniques.

As a method for proliferation of B cells, there has been known a method of culturing B cells in the presence of a CD40 ligand (CD40L) and cytokine such as interleukin (IL)-4 (for example, Patent Literature 1 and Non Patent Literature 1).

Moreover, the germinal center is a histological structure formed as a result that naive B cells, which had been uncontacted with antigens, have been contacted with antigens, and have thereby proliferated. It has been known that class switching or somatic hypermutation would take place in the B cells in the germinal center. For example, Non Patent Literature 2 discloses that, when splenic B cells are cultured together with IL-4 and an anti-μHc antibody in the presence of fibroblasts in which BAFF and CD40L have been allowed to express simultaneously, almost all of the B cells exhibit a germinal center-like phenotype, and as a result, about a half thereof is class-switched to IgG1, and that if IL-4 is then replaced with IL-21, IgE-positive cells increase.

Patent Literature 2 discloses a method for producing an antigen-specific B cell population comprising IgG-positive B cells specific to specific antigens, wherein the method comprises culturing IgG-positive B cells together with the specific antigens in the presence of IL-21, while giving stimulation mediated by CD40, a BAFF receptor and Fas to the cells, and then selecting antigen-specific B cells specific to the specific antigens from the cultured cells, so as to obtain an antigen-specific B cell population comprising IgG-positive B cells specific to the specific antigens.

Patent Literature 3 discloses a method of stabilizing a B cell line, comprising a step of obtaining B cells, a step of increasing the expression of BCL-6 in the B cells, and a step of maintaining the cells in an environment in which the cells can be replicated.

Patent Literature 4 discloses a method of influencing the stability of antibody-producing cells, comprising a stage of directly or indirectly influencing the amounts of expression products of BCL6 and/or Blimp-1 in the antibody-producing cells.

Patent Literature 5 discloses a non-human animal that is characterized in that the expression of a bach2 gene is artificially suppressed, and that IgM and/or IgM-producing hybridomas can be produced at a high frequency by using the aforementioned animal.

PRIOR ART LITERATURES

Patent Literatures

Patent Literature 1: JP Patent Publication (Kohyo) No. 9-512441 A (1997)
Patent Literature 2: JP Patent Publication (Kokai) No. 2011-92142 A
Patent Literature 3: JP Patent Publication (Kokai) No. 2009-142292 A
Patent Literature 4: JP Patent Publication (Kokai) No. 2013-99358 A
Patent Literature 5: International Publication WO No. 2005/110433

Non Patent Literatures

Non Patent Literature 1: J Exp Med. 1992 Vol. 176(6): pp. 1543-1550
Non Patent Literature 2: Abstracts of the Annual Meetings of the Japanese Society for Immunology, 2007, Vol. 37, p. 259, 3-F-W41-16-O/P

SUMMARY OF INVENTION

Object to be Solved by the Invention

A method for highly selectively obtaining only B cells capable of generating IgG antibodies exhibiting a high affinity for specific antigens in a short time, regardless of whether the B cells are naive B cells or B cells after coming into contact with antigens, has not yet been discovered. Accordingly, it is an object of the present invention to provide a method for easily producing an antigen-specific B cell population comprising IgG-positive B cells specific to a specific antigen. In addition, it is another object of the present invention to provide a B cell population produced by the above-described method for producing a B cell population, and a method for producing a monoclonal antibody by applying the above-described method for producing a B cell population.

Means for Solving the Object

As a result of intensive studies directed towards achieving the aforementioned objects, the present inventors have found that B cells, in which the expression of a Bach2 gene has been increased by introduction of the Bach2 gene therein, are cultured in the presence of a means for acting on CD40 and/or a BAFF receptor, so that a B cell population can be cultured at a high growth rate for a long period of time, thereby completing the present invention.

Specifically, according to the present invention, the following inventions are provided.

[1] A method for producing a B cell population, comprising culturing B cells, in which the expression of a Bach2 gene has been increased, in the presence of a means for acting on CD40 and/or a BAFF receptor.

[2] The method for producing a B cell population according to the above [1], wherein the B cells, in which the expression of a Bach2 gene has been increased, are cells which are obtained by introduction of the Bach2 gene into the B cells.

[3] The method for producing a B cell population according to the above [2], wherein the Bach2 gene is any one gene of the following (a) to (d):

(a) a gene consisting of a nucleotide sequence encoding the amino acid sequence(s) shown in SEQ ID NO: 1 and/or SEQ ID NO: 2;

(b) a gene consisting of a nucleotide sequence encoding an amino acid sequence having a sequence identity of 90% or more with the amino acid sequence(s) shown in SEQ ID NO: 1 and/or SEQ ID NO: 2, and having functions equivalent to those of the Bach2 gene;

(c) a gene consisting of a nucleotide sequence encoding an amino acid sequence comprising a deletion, insertion, substitution and/or addition of one or multiple amino acids, with respect to the amino acid sequence(s) shown in SEQ ID NO: 1 and/or SEQ ID NO: 2, and having functions equivalent to those of the Bach2 gene; and (d) a gene hybridizing under stringent conditions with a gene having a nucleotide sequence complementary to the nucleotide sequence encoding the amino acid sequence(s) shown in SEQ ID NO: 1 and/or SEQ ID NO: 2, and having functions equivalent to those of the Bach2 gene.

[4] The method for producing a B cell population according to the above [2] or [3], wherein the Bach2 gene is introduced into B cells by using a virus vector.

[5] The method for producing a B cell population according to the above [4], wherein the virus vector is a retrovirus vector, a lentivirus vector, an adenovirus vector, or an adeno-associated virus vector.

[6A] The method for producing a B cell population according to any one of the above [1] to [5], wherein the B cells are mouse cells, and the specific growth rate obtained from the 9th day to the 13th day after introduction of the Bach2 gene into the B cells is 0.6 (1/day) or more.

[7A] The method for producing a B cell population according to the above [6A], wherein the B cells are mouse cells, and the specific growth rate obtained from any one or more of the 9th day to the 17th day, the 9th day to the 22nd day, the 9th day to the 27th day, the 9th day to the 32nd day, and the 9th day to the 38th day after introduction of the Bach2 gene into the B cells is 0.6 (1/day) or more.

[8A] The method for producing a B cell population according to the above [6A] or [7A], wherein the B cells are mouse cells, the specific growth rate obtained from any one or more of the 13th day to the 17th day, the 17th day to the 22nd day, and the 22nd day to the 27th day after introduction of the Bach2 gene into the B cells is 0.6 (1/day) or more, and the specific growth rate obtained from any one or more of the 27th day to the 32nd day and the 32nd day to the 38th day after introduction of the Bach2 gene into the B cells is 0.4 (1/day) or more.

[6B] The method for producing a B cell population according to any one of the above [1] to [5], wherein the B cells are human cells, and the specific growth rate obtained from the 12th day to the 18th day after introduction of the Bach2 gene into the B cells is 0.1 (1/day) or more.

[7B] The method for producing a B cell population according to the above [6B], wherein the B cells are human cells, and the specific growth rate obtained from any one or more of the 12th day to the 24th day and the 12th day to the 30th day after introduction of the Bach2 gene into the B cells is 0.2 (1/day) or more.

[8B] The method for producing a B cell population according to the above [6B] or [7B], wherein the B cells are human cells, and the specific growth rate obtained from any one or more of the 18th day to the 24th day and the 24th day to the 30th day after introduction of the Bach2 gene into the B cells is 0.15 (1/day) or more.

[9] The method for producing a B cell population according to any one of the above [1] to [8], wherein the means for acting on CD40 and/or a BAFF receptor is any one or more of a structure that presents CD40L and/or BAFF, a stimulating factor for CD40, and a stimulating factor for BAFF receptor.

[10] The method for producing a B cell population according to the above [9], wherein the structure is any one of a carrier, a feeder cell, an extracellular matrix, a biological tissue, and an organ.

[11] The method for producing a B cell population according to the above [9] or [10], wherein the stimulating factor for CD40 or the stimulating factor for BAFF receptor is any one of an anti-CD40 antibody, secretory CD40L, an anti-BAFF receptor antibody, and secretory BAFF.

[12] The method for producing a B cell population according to any one of the above [9] to [11], wherein the concentration of the stimulating factor for CD40 contained in the medium, in which the B cells are cultured, is 10 ng/mL or more.

[13] The method for producing a B cell population according to any one of the above [9] to [12], wherein the concentration of the stimulating factor for BAFF receptor contained in the medium, in which the B cells are cultured, is 10 ng/mL or more.

[14] The method for producing a B cell population according to any one of the above [1] to [13], wherein a step of culturing B cells, in which the expression of a Bach2 gene has been increased, in the presence of a means for acting on CD40 and/or a BAFF receptor, is a step of culturing the B cells in the presence of a means for acting on CD40 and/or a BAFF receptor and a means for acting on an IL-21 receptor.

[15] The method for producing a B cell population according to any one of the above [1] to [13], wherein a step of culturing B cells, in which the expression of a Bach2 gene has been increased, in the presence of a means for acting on CD40 and/or a BAFF receptor, is a step of culturing the B cells in the presence of a means for acting on CD40 and/or a BAFF receptor, a means for acting on an IL-21 receptor, and IL-4 and/or IL-2.

[16] The method for producing a B cell population according to the above [14] or [15], wherein the means for acting on an IL-21 receptor is IL-21 and/or an anti-IL-21 receptor antibody.

[17] The method for producing a B cell population according to the above [16], wherein the concentration of IL-21 and/or an anti-IL-21 receptor antibody contained in the medium, in which the B cells are cultured, is 1 ng/mL or more.

[18] The method for producing a B cell population according to the above [15], wherein the concentration of IL-4 contained in the medium, in which the B cells are cultured, is 5 ng/mL or more.

[19] The method for producing a B cell population according to the above [15] or [18], wherein the concentration of IL-2 contained in the medium, in which the B cells are cultured, is 2.5 U/mL or more.

[20] The method for producing a B cell population according to any one of the above [2] to [5], wherein the B cells are cultured in the presence of a means for acting on CD40 and/or a BAFF receptor, and in the presence of IL-4, or IL-4 and IL-2, before the Bach2 gene is introduced into the B cells.

[21] The method for producing a B cell population according to the above [20], wherein the concentration of IL-4 contained in the medium, in which the B cells are cultured, is 5 ng/mL or more.

[22] The production method according to the above [20] or [21], wherein the concentration of IL-2 contained in the medium, in which the B cells are cultured, is 2.5 U/mL or more.

[23] The method for producing a B cell population according to any one of the above [1] to [22], wherein a step of culturing B cells, in which the expression of a Bach2 gene has been increased, in the presence of a means for acting on CD40 and/or a BAFF receptor, is a step of culturing the B cells in the absence of FAS-mediated stimulation.

[24] The method for producing a B cell population according to the above [23], which further comprises culturing, in the presence of FAS-mediated stimulation, the B cells that have been cultured in the absence of FAS-mediated stimulation.

[25] A B cell population produced by the production method according to any one of the above [1] to [24].

[26] The B cell population according to the above [25], wherein the B cells have a Bach2 gene incorporated into a virus vector.

[27] The B cell population according to the above [25] or [26], wherein the B cells are mouse cells, and the specific growth rate obtained from the 9th day to the 13th day after introduction of the Bach2 gene into the B cells is 0.6 (1/day) or more.

[28] The B cell population according to the above [25] or [26], wherein the B cells are human cells, and the specific growth rate obtained from the 12th day to the 18th day after introduction of the Bach2 gene into the B cells is 0.1 (1/day) or more.

[29] A method for producing a monoclonal antibody, wherein a B cell population produced by the production method according to any one of the above [1] to [24] is used.

Advantageous Effects of Invention

According to the present invention, an antigen-specific B cell population comprising IgG-positive B cells that are specific to a specific antigen can be easily produced.

BRIEF DESCRIPTION OF DRAWINGS

FIG. 1 shows the cumulative growth rate of mouse B cells of the long-term culture in which a retrovirus vector has been used, wherein the value at the 5th day of the B cells is defined as 1.

FIG. 2 shows the specific growth rate of the mouse B cells from the 9th day of the long-term culture of the B cells, in which a retrovirus vector has been used.

FIG. 3 shows the specific growth rate of mouse B cells in each period in the long-term culture of the B cells, in which a retrovirus vector has been used.

FIG. 4 shows the cumulative growth rate of human B cells of the long-term culture in which a retrovirus vector has been used, wherein the value at the 6th day of the B cells is defined as 1.

FIG. 5 shows the specific growth rate of human B cells from the 12th day of the long-term culture of the B cells, in which a retrovirus vector has been used.

FIG. 6 shows the specific growth rate of human B cells in each period in the long-term culture of the B cells, in which a retrovirus vector has been used.

DESCRIPTION OF EMBODIMENTS

Hereinafter, the present invention will be described more in detail.

The method for producing a B cell population of the present invention comprises culturing B cells, in which the expression of a Bach2 gene has been increased, in the presence of a means for acting on CD40 and/or a BAFF receptor.

The B cells, in which the expression of a Bach2 gene has been increased, may be either cells obtained by introducing a Bach2 gene into B cells, or cells obtained by increasing the expression level or abundance of a Bach2 gene originally possessed by B cells.

The method of increasing the expression level or abundance of a Bach2 gene originally possessed by B cells is not particularly limited. Examples of such a method include: a method of introducing a Menin gene (Nature Communications, 5: 3555, DOI: 10: 1038. ncomms4555) into B cells; a method of inhibiting the nuclear export of Bach2 by addition of leptomycin B (LMB) and allowing the Bach2 to be localized in the nucleus; and a method of adding an inhibitor for inhibiting ubiquitination of Bach2 and decomposition by proteasome to the B cells.

The Bach2 gene to be introduced into B cells is preferably a gene described in any one of the following (a) to (d):
(a) a gene consisting of a nucleotide sequence encoding the amino acid sequence(s) shown in SEQ ID NO: 1 and/or SEQ ID NO: 2;
(b) a gene consisting of a nucleotide sequence encoding an amino acid sequence having a sequence identity of 90% or more with the amino acid sequence(s) shown in SEQ ID NO: 1 and/or SEQ ID NO: 2, and having functions equivalent to those of the Bach2 gene;

(c) a gene consisting of a nucleotide sequence encoding an amino acid sequence comprising a deletion, insertion, substitution and/or addition of one or multiple amino acids, with respect to the amino acid sequence(s) shown in SEQ ID NO: 1 and/or SEQ ID NO: 2, and having functions equivalent to those of the Bach2 gene; and (d) a gene hybridizing under stringent conditions with a gene having a nucleotide sequence complementary to the nucleotide sequence encoding the amino acid sequence(s) shown in SEQ ID NO: 1 and/or SEQ ID NO: 2, and having functions equivalent to those of the Bach2 gene.

The amino acid sequence shown in SEQ ID NO: 1 is the amino acid sequence of mouse Bach2, and the amino acid sequence shown in SEQ ID NO: 2 is the amino acid sequence of human Bach2.

The sequence identity with the amino acid sequence(s) shown in SEQ ID NO: 1 and/or SEQ ID NO: 2 is preferably 90% or more, more preferably 93% or more, further preferably 95% or more, and particularly preferably 98% or more. The sequence identity of an amino acid sequence is indicated as a value obtained by comparing an amino acid sequence to be evaluated with the amino acid sequence(s) shown in SEQ ID NO: 1 and/or SEQ ID NO: 2, then dividing the number of amino acids matched between both sequences by the total number of compared amino acids, and then multiplying the obtained value by 100.

The gene consisting of a nucleotide sequence encoding an amino acid sequence comprising a deletion, insertion, substitution and/or addition of one or multiple amino acids, with respect to the amino acid sequence(s) shown in SEQ ID NO: 1 and/or SEQ ID NO: 2, can be prepared in accordance with a known method described in "Current Protocols in Molecular Biology (John Wiley and Sons, Inc., 1989)," etc.

In the present description, the phrase "having functions equivalent to those of the Bach2 gene" is used to mean that a gene has functions equivalent to those of the gene consisting of a nucleotide sequence encoding the amino acid sequence(s) shown in SEQ ID NO: 1 and/or SEQ ID NO: 2, and it means, for example, that a gene exhibits a cell growth function equivalent to that of the aforementioned gene consisting of a nucleotide sequence encoding the amino acid sequence(s) shown in SEQ ID NO: 1 and/or SEQ ID NO: 2, when it is introduced into B cells. Moreover, as one function of the Bach2 gene, it has been known that the expression product of the Bach2 gene binds to MARE (Maf-recognition element) located upstream of the promoter of a Blimp1 gene and an IRF binding sequence in the 5th intron, so as to suppress transcription of the Blimp1 gene. Thus, the phrase "having functions equivalent to those of the Bach2 gene" may also mean that a gene has the function of suppressing transcription of the Blimp1 gene, as in the case of the Bach2 gene.

The amino acid sequence modified by a deletion, insertion, substitution and/or addition of amino acid(s) may be either an amino acid sequence comprising only one type of modification (e.g., a substitution), or an amino acid sequence comprising two or more modifications (e.g., a substitution and an insertion). In the case of a substitution, the amino acid(s) used in the substitution are preferably amino acids having properties similar to those of the amino acids before substitution (i.e., cognate amino acids). Herein, the following amino acids in each group are considered to be such cognate amino acids.

(Group 1: neutral non-polar amino acids) Gly, Ala, Val, Leu, Ile, Met, Cys, Pro, and Phe (Group 2: neutral polar amino acids) Ser, Thr, Gln, Asn, Trp, and Tyr (Group 3: acidic amino acids) Glu and Asp (Group 4: basic amino acids) His, Lys, and Arg.

The above-described multiple amino acids means, for example, 60, preferably 20, more preferably 15, even more preferably 10, further preferably 5, 4, or 3, and particularly preferably 2 or less amino acids.

The term "gene hybridizing under stringent conditions with a gene having a nucleotide sequence complementary to the nucleotide sequence encoding the amino acid sequence(s) shown in SEQ ID NO: 1 and/or SEQ ID NO: 2" is used to mean DNA obtained by applying a colony hybridization method, a plaque hybridization method, a Southern hybridization method, etc., under stringent conditions, using, as a probe, DNA consisting of a nucleotide sequence complementary to the nucleotide sequence encoding the amino acid sequence(s) shown in SEQ ID NO: 1 and/or SEQ ID NO: 2, or a portion thereof.

Hybridization can be carried out herein in accordance with a method described in "Molecular Cloning, A laboratory manual, second edition (Cold Spring Harbor Laboratory Press, 1989)," etc. Herein, the DNA hybridizing with another DNA under stringent conditions can be, for example, a DNA that can be obtained by carrying out hybridization in the presence of 0.7 to 1.0 M NaCl at 65° C., using a filter on which a colony- or plaque-derived DNA is immobilized, and then washing the filter with a 2×SSC solution (wherein the composition of a 1×SSC solution consists of 150 mM sodium chloride and 15 mM sodium citrate) at 65° C. It is a DNA that can be obtained by washing the filter, preferably with a 1×SSC solution at 65° C., more preferably with a 0.5×SSC solution at 65° C., further preferably with a 0.2×SSC solution at 65° C., and most preferably with a 0.1×SSC solution at 65° C.

The conditions for the hybridization are as described above. However, the hybridization conditions are not particularly limited thereto. It is considered that there are multiple factors, such as temperature and salt concentration, which have influence on stringency of the hybridization. A person skilled in the art could appropriately select these factors to realize the optimal stringency.

In order to introduce a Bach2 gene into B cells, a recombinant vector having such a Bach2 gene may be constructed, and this recombinant vector may be then introduced into B cells. Examples of the vector include a virus vector, a plasmid vector, and a liposome vector (for example, a cationic liposome vector). Specific examples of the virus vector include a retrovirus vector (for example, a lentivirus vector such as an HIV vector), an adenovirus vector, an adeno-associated virus vector, a herpesvirus vector, a Sendai virus vector, and a baculovirus vector. The vector is preferably a virus vector, more preferably a retrovirus vector (for example, a lentivirus vector such as an HIV vector), an adenovirus vector or an adeno-associated virus vector, and particularly preferably a retrovirus vector (for example, a lentivirus vector such as an HIV vector).

The vector may comprise a sequence regulating the expression of a Bach2 gene (for example, a promoter sequence, a terminator sequence, or an enhancer sequence), a gene marker for selecting host cells (for example, a neomycin resistance gene or a kanamycin resistance gene), and the like, as well as the Bach2 gene. As a method of constructing the vector, a method that has been commonly used in the field of gene engineering can be used.

As a method of introducing a vector comprising a Bach2 gene into B cells, for example, in the case of using a virus vector, the introduction can be carried out by infection. In the case of using a plasmid vector, an electroporation method, a calcium phosphate method, a lipofection method, or the like can be applied.

A level of increase in the expression of a Bach2 gene is not particularly limited, as long as the effects of the present invention can be obtained. With regard to such an increased level, the expression level of the Bach2 gene is preferably 1.5 times or more, and more preferably 2 times or more, higher than that in the original B cells.

The B cells used in the present invention are preferably IgG-positive B cells, namely, B cells each having IgG on the surface thereof. The IgG-positive B cells can be obtained from a cell population comprising B cells, based on the presence or absence of reactivity with IgG antibody.

The cell population comprising B cells used in the present invention is not particularly limited, as long as it is a cell population derived from peripheral blood cells, bone marrow cells, or lymphoid organs, such as, for example, splenic cells. In addition, the IgG-positive B cells may be either antigen-unreacted naive B cells, or B cells after contact with antigens. Herein, the term "naive B cells" is used in the present description to generally indicate mature B cells that have not been reacted with antigens. The naive B cells herein correspond to CXCRS-positive and CD40-positive antigen-presenting cells. Moreover, the cell population used in the present invention preferably has an IL-21 receptor (IL-21R) and CD40, a BAFF receptor (BAFF-R), or it also preferably has Fas. Furthermore, the present cell population preferably comprises IgG-positive B cells capable of recognizing antigens. Further, the present cell population may also comprise B cells at a different stage in the differentiation process, or various other types of cells, unless it impairs the objects of the present invention. From the viewpoint of selection efficiency by culture, B cells other than IgG-positive B cells, such as, for example, IgE-positive cells or CD138-positive (plasma) cells, or cells other than B cells, such as, for example, T cells, monocytes or NK cells, are preferable eliminated.

In the present invention, the cell population may be a cell population derived from an organism whose immune system has been established. Examples of the such organism include primates such as a human or a monkey and ungulates such as a swine, a bovine or a horse, as mammals, rodents as small mammals, such as a mouse, a rat or a rabbit, and birds such as a chicken or a quail. The origins of the present cell population are preferably rodents and primates, and examples of the origins include a mouse and a human. To a method of preparing a cell population from biological tissues such as spleen, ordinary conditions for preparation of B cell population may be directly applied. In addition, the present cell population is not limited to an organism-derived cell population, and it may also be an established B cell line.

To the culture of a cell population comprising B cells, ordinary culture conditions, in which a medium used in the culture of B cells is used, may be generally applied. Examples of the medium include Dulbecco's Modified Eagle's Medium (DMEM) and RPMI1640. To these culture media, various types of additives applicable to ordinary cell culture, such as serum, various types of vitamins, and various types of antibiotics, may be generally added. As culture conditions such as a culture temperature, culture conditions generally used for B cells may be directly applied. Examples of such culture conditions include 37° C. and 5% $CO_2$.

The seeding density, at which a cell population is seeded in a culture medium, is different depending on the origin of the cell population, the conditions of cells prepared from tissues, and the number of days in which the culture is carried out in a single culture system. The seeding density is generally $1 \times 10^2$ cells to $1 \times 10^7$ cells/$cm^2$, and preferably $1 \times 10^3$ cells to $1 \times 10^7$ cells/$cm^2$. In particular, since human B cells have a high proliferation rate when the cell culture is initiated at a high density, the cell density may be preferably set from $1 \times 10^4$ cells to $1 \times 10^7$ cells/$cm^2$. If the cell density is within this range, the cells can be prevented from being in a hyperprolilferation state after the culture for approximately 4 days.

When intracellular signals are to be generated in the presence of IL-21 by stimulation mediated by CD40 and a BAFF receptor, the B cells used in the present invention preferably have an IL-21 receptor (IL-21R), CD40, and a BAFF receptor (BAFF-R). The stimulation to these molecules is not particularly limited, as long as it recognizes these molecules from the outside thereof and generates intracellular signals inside of IgG-positive B cells having CD40 and a BAFF receptor.

In the present invention, the means for acting on CD40 and/or a BAFF receptor can be, for example, any one or more of a structure that presents a CD40 ligand (CD40L) and/or BAFF, a stimulating factor for CD40, and a stimulating factor for BAFF receptor.

Examples of the stimulating factor for CD40 include an anti-CD40 antibody and secretory CD40L. CD40L is a ligand for CD40, and the amino acid sequence of CD40L has been known (see, for example, Nature, Vol. 357, pp. 80-82 (1992), and EMBO J., Vol. 11, pp. 4313-4321 (1992)). In the present invention, it is adequate if the sequence of CD40L is preserved to such an extent that the binding ability of an active domain thereof associated with receptor-binding ability is not lost. For example, if the active domain of certain CD40L shows homology of 80% or more at the amino acid sequence level with that of the original CD40L, it can be used in the present invention. Such CD40L may be isolated from naturally expressing cells, or may also be synthesized based on the known amino acid sequence. In addition, the CD40L may have a form capable of giving signals corresponding to the presence of CD40L to B cells in a culture system. The CD40L may have a free form, or a membrane-bound form.

In order to form a cell population comprising IgG-positive B cells, the stimulating factor for CD40, such as free-form CD40L, may be present in a culture system in a concentration in which B cells are able to maintain their proliferation. Such a concentration may be, for example, from 10 ng/mL to 10 μg/ml. Taking into consideration a relative decrease attended with proliferation of B cells, the concentration can be set from 50 ng/mL to 10 μg/ml.

Examples of the stimulating factor for BAFF receptor include an anti-BAFF receptor antibody and secretory BAFF.

BAFF (B cell activation factor: B cell activation factor belonging to the tumor necrosis factor family) is a TNF analog molecule that has been known to be associated with proliferation and differentiation of B cells that have reacted with antigens. The amino acid sequence of BAFF has already been known (for example, J Exp Med, Vol. 189, pp. 1747-1756 (1999), Science, Vol. 285, pp. 260-263 (1999), and J Bio Chem, Vol. 274, pp. 15978-15981, (1999)). In the present invention, it is adequate if the sequence of BAFF is preserved to such an extent that the binding ability of an active domain thereof associated with receptor-binding ability is not lost. For example, if the active domain of certain BAFF shows homology of 80% or more at the amino acid sequence level with that of the original BAFF, it can be used in the present invention. Such BAFF may be isolated from naturally expressing cells, or may also be synthesized based on the known amino acid sequence. In addition, the BAFF may have a form capable of giving signals corresponding to the presence of BAFF to IgG-positive B cells in a culture system. The BAFF may have a free form (namely, secretory form), or a membrane-bound form.

In order to form a cell population comprising IgG-positive B cells, the stimulating factor for BAFF receptor, such as free-form BAFF, may be present in a culture system in a concentration in which B cells are able to maintain their proliferation. Such a concentration may be, for example, from 10 ng/mL to 10 µg/ml. From the viewpoint that a higher survival supporting activity can be expected if the stimulating factor for BAFF receptor is present at a higher concentration, the concentration can be preferably set from 50 ng/mL to 10 µg/ml.

The step of culturing B cells, in which the expression of a Bach2 gene has been increased, in the presence of a means for acting on CD40 and/or a BAFF receptor, may be either a step of culturing the B cells in the absence of FAS-mediated stimulation, or a step of culturing the B cells in the presence of FAS-mediated stimulation. Otherwise, B cells cultured in the absence of FAS-mediated stimulation may be then cultured in the presence of FAS-mediated stimulation. In order to selectively concentrate B cells, a step of culturing the B cells in the presence of a means for acting on CD40 and/or a BAFF receptor is preferably carried out, before culturing the B cells in the presence of FAS-mediated stimulation.

The Fas ligand (FasL) is a death factor belonging to the TNF family, namely, a cytokine exhibiting an apoptosis-inducing activity. The amino acid sequence of the Fas ligand has been known (see, for example, Cell, Vol. 75, pp. 1169-1178 (1993)). In the present invention, it is adequate if the sequence of FasL is preserved to such an extent that the binding ability of an active domain thereof associated with receptor-binding ability is not lost. For example, if the active domain of certain FasL shows homology of 80% or more at the amino acid sequence level with that of the original FasL, it can be used in the present invention. Such FasL may be isolated from naturally expressing cells, or may also be synthesized based on the known amino acid sequence. In addition, the FasL may have a form capable of giving signals corresponding to the presence of Fas to IgG-positive B cells in a culture system. The FasL may have a free form, or a membrane-bound form so long as it can give intracellular signals. FasL may be generally present in a culture system in a concentration capable of inducing apoptosis to B cells, and such a concentration is, for example, 10 ng/mL to 10 µg/ml. In addition, from the viewpoint of inducing suppression of cell death by antigen stimulation, the concentration can be preferably set from 10 ng/mL to 1 µg/ml.

As in the case of the above-mentioned cell population, examples of the origins of CD40L, BAFF and FasL include primates and ungulates as mammals, rodents as small mammals, and birds. The CD40L, BAFF and FasL are preferably derived from rodents and mammals, and examples or such rodents and mammals include humans and mice. In addition, the CD40L, BAFF and FasL may be derived either from the same species as that of the above-described cell population as a presentation target, or from species different from that of the above-described cell population.

An antibody against CD40, a BAFF receptor (BAFF-R) or Fas, or an antibody fragment thereof, can be obtained according to a method known in the present technical field. The type of such an antibody is not particularly limited, as long as it is an antibody having an ability to bind to CD40, a BAFF receptor (BAFFR) or Fas. Such an antibody or an antibody fragment may have a form, in which it is presented on the surface of a carrier, or may also have a free form or a solubilized form, in which it is not immobilized on the surface of a carrier.

From the viewpoint of certainly giving intracellular signals to B cells in a culture system, CD40L, BAFF or FasL preferably has a form, in which it is presented on a structure. The structure is preferably any one of a carrier, a feeder cell, an extracellular matrix, a biological tissue, and an organ. The carrier used to present each molecule on the surface thereof is not particularly limited, as long as it is generally used to present the aforementioned molecule on the surface thereof. Examples of such a carrier include an artificial lipid bilayer, a plastic such as polystyrene or polyethylene terephthalate, collagen, nylon, a polysaccharide such as nitrocellulose, agar, agarose or sepharose, a paper, and a glass. The shape of such a carrier is not particularly limited, and all shapes such as a sheeted, planar, spherical, spongy, or fibrous shape, may be adopted. From the viewpoint of reliable selectivity of cells, the structure is preferably a feeder cell. Examples of cells that can be used as feeder cells include fibroblasts, epithelial cells (e.g., HeLa cells), embryonic kidney cells (e.g., HEK293, etc.), and follicular dendritic cells. From the viewpoint of high proliferation rate, large cell surface area, and easy removal of feeder cells, fibroblasts are preferable among these cells.

A feeder cell, on the surface of which CD40L, BAFF, and as desired, FasL are presented, can be produced by a person skilled in the art according to a genetic recombination technique or the like, based on the known sequences of CD40L, BAFF, and FasL. As in the case of the aforementioned cell population, examples of the origin of feeder cells include primates and ungulates as mammals, rodents as small mammals, and birds. Preferred examples include rodents and mammals, such as mice and humans. Moreover, such feeder cells may be either cells derived from the same species as the above-described cell population as a presentation target, or cells derived from different species.

In the present invention, B cells producing desired IgG may be selected by presenting a specific antigen to IgG-positive B cells. The term "specific antigen" is used herein to mean an antigen, for which the antigen-specific IgG-positive B cells of interest exhibit an affinity, and the specific antigen is appropriately selected depending on purpose. The type of the antigen is not particularly limited, as long as it exhibits antigenicity, and examples of such an antigen include nucleic acids such as DNA or RNA, a sugar chain, a lipid, an amino acid, a peptide, a protein, a hapten, and a low-molecular-weight compound. These substances may be presented in a form in which B cells are able to recognize the substances, and such a form may be either a free form or a carrier-immobilized form. From the viewpoint of secure presentation of an antigen to B cells, the antigen is preferably immobilized on a carrier.

In order to enhance the antigen recognition of IgG-positive B cells, in addition to a form in which the antigen alone is used, the antigen may also have forms known in the present technical field, such as a form in which a known auxiliary molecule is added to the antigen, or a form in which the antigen binds to an antibody molecule.

When such a binding form to an antibody molecule or a fusion protein consisting of a protein antigen and an antibody F region is applied to antigen presentation, an anchorage for presenting an antigen on the surface of a carrier, such as an Fc receptor molecule, protein A or protein G, may be further used. In addition, a fusion protein consisting of a protein binding to a constituent of a carrier and an antigen protein may also be used. Moreover, when a membrane-type protein is presented as an antigen, the gene of the protein may be introduced using an expression vector into a cell used as a carrier, and it may be then expressed therein. In the case of other proteins, they may be introduced into a cell used as a carrier, using an expression vector capable of expressing a fusion protein consisting of a suitable signal peptide (which is not necessary in the case of a secretory protein) and a suitable transmembrane region (e.g. a region of MHC class I), and may be then expressed therein.

From the viewpoint of selection efficiency of selecting antigen-specific B cells of interest, it is more preferable that CD40L, BAFF or FasL, and an antigen be presented on feeder cells. It is to be noted that CD40L, BAFF, and as desired FasL, and an antigen may not be necessarily present on the same feeder cell, if they allow IgG-positive B cells to generate intracellular signals.

In the present invention, when B cells, in which the expression of a Bach2 gene has been increased, are cultured in the presence of a means for acting on CD40 and/or a BAFF receptor, the culture is preferably carried out in the presence of a means for acting on an IL-21 receptor.

As such a means for acting on an IL-21 receptor, IL-12 or an anti-IL-21 receptor antibody can be used.

IL-21 may be derived from the nature, or may also be a biotechnologically obtained recombinant IL-21. As in the case of the aforementioned cell population, examples of the origin of IL-21 include primates and ungulates as mammals, rodents as small mammals, and birds. These molecules are each derived from, preferably, rodents and mammals, such as mice and humans. Moreover, such molecules may be either molecules derived from the same species as the above-described cell population as a presentation target, or molecules derived from different species.

The concentration of IL-21 and/or an anti-IL-21 receptor antibody contained in a medium for culturing B cells is not particularly limited, as long as it may be an amount capable of proliferating IgG-positive B cells having an affinity for a specific antigen. In general, the concentration is set at preferably 1 ng/mL to 1 μg/ml, and more preferably 100 ng/mL to 1 μg/ml.

Although it depends conditions such as seeding density and cell type, the selection step is generally carried out for a half day or more after initiation of the selection step, from the viewpoint of secure selection, and it may also be carried out for 1 to 3 days, and preferably for 1 to 2 days, from the viewpoint of secure selection. The time required for the selection step may also be longer, if the viability of cells can be maintained, and thus, antigen-specific IgG-positive B cells having a higher affinity for a specific antigen can be obtained by culturing the cells for a longer period of time.

Moreover, in order to improve the affinity of B cells for an antigen, the selection step may be repeatedly carried out, while changing feeder cells. In such a case, in order to proliferate IgG-positive B cells, the after-mentioned secondary culture is preferably carried out after each selection step. In order to improve the affinity of the B cells for an antigen, it may also be possible to change (decrease) the concentration or valence of the antigen every time the step is repeated. Furthermore, in order to improve the affinity of the B cells for an antigen, it may further be possible to add a culture supernatant obtained from the immediately previous step or an antibody generated in the culture supernatant to a culture system, when the subsequent step is carried out. Thereby, a competition is generated between the B cell receptor and the antibody, so that B cells having a higher-affinity B cell receptor can be selected.

In the present invention, when B cells, in which the expression of a Bach2 gene has been increased, are cultured in the presence of a means for acting on CD40 and/or a BAFF receptor, the culture may be preferably carried out in the presence of IL-4 and/or IL-2. However, from the viewpoint of the ratio of IgG-positive B cells in the obtained cell population, IL-4 is preferably not contained in the culture system.

In the IgG-positive B cells of the present invention having an IL-21 receptor (IL-21R), CD40, and a BAFF receptor (BAFF-R), the presence of these molecules may be confirmed based on, for example, reactivity by using an antibody or the like. However, from the viewpoint of the time required for preparation of the cells and the cell density of the IgG-positive B cells of interest, the present IgG-positive B cells may be preferably obtained by a method which comprises a primary culture step of culturing a cell population comprising B cells in the presence of IL-4, while giving stimulation mediated by CD40 and a BAFF receptor to the cells, and a secondary culture step of culturing the cells in the presence of IL-21 (culture steps).

With regard to the aforementioned culture steps, both the primary culture and the secondary culture can be carried out, while giving stimulation mediated by CD40 and a BAFF receptor to the cells. As in the case of the selection step, the stimulation mediated by CD40 and a BAFF receptor may be carried out, either using antibodies against these molecules, or using CD40L and BAFF. In addition, from the viewpoint of reliably giving the stimulation from these antibodies and molecules to a cell population as a culture target, a carrier having these antibodies or CD40L and BAFF, for example, a feeder cell may be used. With regard to CD40L, BAFF, a carrier and the like, the matter described in the selection step can be directly applied. The carrier and feeder cell used in the culture step may also be referred to as a "carrier for culture" and a feeder cell for culture," respectively.

The IL-4 used in the primary culture may be derived from the nature, or may also be a biotechnologically obtained recombinant IL-4. From the viewpoint of effective proliferation of B cells, the concentration of IL-4 is set at preferably 1 ng/mL to 100 ng/mL, more preferably 5 ng/mL to 100 ng/mL, and further preferably 10 ng/mL to 50 ng/mL.

In the primary culture, other cytokines, as well as IL-4, may be used depending on the type or origin of the B cell population as a culture target. For example, in a case where IL-2 is used in combination with IL-4, the concentration of IL-2 is preferably 1 unit/ml to 1000 units/ml, more preferably 2.5 units/ml to 1000 units/ml, further preferably 2.5 units/ml to 500 units/ml, and particularly preferably 10 units/ml to 100 units/ml.

The seeding density of cells upon initiation of the primary culture is not particularly limited. The seeding density is different depending on the origin of a cell population, the condition of cells prepared from tissues, or the number of days for culture performed in a single culture system. The seeding density may be set at generally $1 \times 10^2$ cells to $1 \times 10^6$ cells/cm$^2$, and preferably $1 \times 10^3$ cells to $1 \times 10^6$ cells/cm$^2$. From the viewpoint of the growth rate of the B cell population, the primary culture may be generally carried out for 2 to 8 days after initiation of the culture, although it depends on seeding density. From the viewpoint of the density of IgG-positive B cells in the cell population, the time required for the primary culture is preferably for 3 to 6 days, and more preferably for 3 to 5 days.

Upon initiation of the secondary culture, a predetermined amount of IL-21 may be added to the culture system after completion of the primary culture. Otherwise, cells may be recovered from the culture system after completion of the primary culture, and may be then transferred into an IL-21-containing medium that does not contain IL-4, before initiation of the secondary culture. From the viewpoint of the growth rate of IgG-positive B cells in the secondary culture and suppression of the mixing of IgE-positive B cells into the obtained cell population, the secondary culture is most preferably carried out in a medium that contains IL-21 and does not contain IL-4.

As in the case of the aforementioned cell population, examples of the origins of the IL-4 and IL-21 used in the present invention include primates and ungulates as mammals, rodents as small mammals, and birds. These molecules are each derived from, preferably, rodents and mammals, such as mice and humans. Moreover, they may be either molecules derived from the same species as the above-described cell population as a presentation target, or cells derived from different species.

After completion of the secondary culture, in order to reliably enhance the concentration of B cells of interest, cells other than IgG-positive B cells are preferably removed. Examples of the cells to be removed include IgE-positive B cells, CD138-positive plasma cells, and feeder cells (if they are present). These cells can be removed from the culture by a known technique of using an antibody against an original surface antigen present on the surface of the cell, etc.

Moreover, in the secondary culture, other cytokines, as well as IL-21, can be used depending on the type or origin of the B cell population as a culture target. For example, in a case where IL-2 is used in combination with IL-21, the concentration of IL-2 is preferably 1 unit/ml to 1000 units/ml, more preferably 2.5 units/ml to 1000 units/ml, further preferably 2.5 units/ml to 500 units/ml, and particularly preferably 10 units/ml to 100 units/ml.

In the method for producing a B cell population of the present invention, the method may be carried out for a period necessary for selecting the antigen-specific IgG-positive cells of interest. Such a period can be changed, as appropriate, depending on the number of IgG-positive B cells upon initiation of the selection step, the type of an antigen used, the condition of feeder cells, or the like. For example, in order to efficiently obtain a cell population of interest, the selection step may be carried out for 1 to 2 days. In a case where the present production method includes a culture step, the primary culture may be carried out for 3 to 5 days, the secondary culture may be carried out for 2 to 5 days, and the selection step may be carried out for 1 to 2 days.

The production method of the present invention may comprise a proliferation step of further proliferating the selected antigen-specific IgG-positive B cells, after completion of the selection step. This proliferation step may be carried out under culture conditions, in which antigen-specific IgG-positive B cells which were selected in the selection step and are specific to specific antigen can be proliferated. From the viewpoint of efficient proliferation of the selected IgG-positive B cells, the cells are preferably cultured together with CD40L and BAFF in the presence of IL-21. As for IL-21 preferably used in the proliferation step, conditions applied to the aforementioned secondary culture or selection step can be directly applied. Also, as for CD40L and BAFF preferably used in the proliferation step, the aforementioned matter can be directly applied.

The proliferation step may be continued for a period that depends on the number of the IgG-positive B cells of interest in the obtained cell population. The proliferation step can be carried out generally for 1 or more days, and preferably for 3 or more days. The time required for the proliferation step may be adjusted, as appropriate, depending on the growth rate and density of the cell population contained in the culture system.

According to the present invention, a B cell population produced by the above-described method for producing a B cell population is provided. The B cell of the present invention preferably has a Bach2 gene incorporated into a virus vector. The B cell population of the present invention preferably has a high specific growth rate, as described later in the present description. As described above, the B cell population of the present invention has a high specific growth rate, and a preferred aspect of the B cell population is specified by determination with the numerical value of such a specific growth rate. It is impossible or impractical to determine the structure itself of the B cell population of the present invention, without depending on the production method thereof. Thus, the B cell population of the present invention is determined by the production method thereof (namely, a method for producing a B cell population, comprising a step of culturing B cells, in which the expression of a Bach2 gene has been increased, in the presence of a means for acting on CD40 and/or a BAFF receptor).

The proliferation of the B cell population of the present invention can be evaluated using a specific growth rate. The specific growth rate is defined as an increase in the amount of cells per unit time, and it is represented by specific growth rate: $\mu=\ln(m_{t2}/m_{t1})/(t2-t1)$. Herein, $m_{t1}$ indicates the number of cells on Day t1, and $m_{t2}$ indicates the number of cells on Day t2 (provided that t2>t1). Accordingly, the unit of the specific growth rate is (cells/cells/day)=(1/day).

Hereafter, with regard to a case where B cells are mouse cells and a case where B cells are human cells, a preferred range of the specific growth rate will be described.

(Case where B Cells are Mouse Cells)

With regard to the method for producing a B cell population according to the present invention and the B cell population obtained by the above-described production method, the specific growth rate on Day 9 to Day 13 after introduction of the Bach2 gene into the B cells is preferably 0.6 (1/day) or more, more preferably 0.8 (1/day) or more, and particularly preferably 1.0 (1/day) or more.

Moreover, the specific growth rate on any one or more of Day 9 to Day 17, Day 9 to Day 22, Day 9 to Day 27, Day 9 to Day 32, and Day 9 to Day 38, after introduction of the Bach2 gene into the B cells is preferably 0.6 (1/day) or more. The specific growth rate on any one or more of Day 9 to Day 17, Day 9 to Day 22, and Day 9 to Day 27 after the gene introduction is preferably 0.6 (1/day) or more, and more preferably 0.8 (1/day) or more. Preferably, the specific growth rate on all of Day 9 to Day 17, Day 9 to Day 22, and Day 9 to Day 27 after the gene introduction is preferably 0.6 (1/day) or more, and more preferably 0.8 (1/day) or more.

The specific growth rate on both of Day 9 to Day 32 and Day 9 to Day 38 after the gene introduction is preferably 0.6 (1/day) or more.

Furthermore, the specific growth rate on any one or more of Day 13 to Day 17, Day 17 to Day 22, and Day 22 to Day 27, after introduction of the Bach2 gene into the B cells is preferably 0.6 (1/day) or more, and the specific growth rate on all of Day 13 to Day 17, Day 17 to Day 22, and Day 22 to Day 27, after the gene introduction is preferably 0.6 (1/day) or more.

Further, the specific growth rate on any one or more of Day 27 to Day 32 and Day 32 to Day 38 after introduction of the Bach2 gene into the B cells is preferably 0.4 (1/day) or more, and the growth rate on both of Day 27 to Day 32 and Day 32 to Day 38 after the gene introduction is preferably 0.4 (1/day) or more.

It is to be noted that the upper limit of the specific growth rate of the above-mentioned mouse B cells is not particularly limited, and in general, it is 2.3 (1/day) or less, or 1.6 (1/day) or less.

(Case where B Cells are Human Cells)

With regard to the method for producing a B cell population according to the present invention and the B cell population obtained by the above-described production method, the specific growth rate on Day 12 to Day 18 after introduction of the Bach2 gene into the B cells is preferably 0.1 (1/day) or more, more preferably 0.13 (1/day) or more, and particularly preferably 0.15 (1/day) or more.

Moreover, the specific growth rate on any one or more of Day 12 to Day 24 and Day 12 to Day 30 after introduction of the Bach2 gene into the B cells is preferably 0.1 (1/day) or more, more preferably 0.13 (1/day) or more, and further preferably 0.15 (1/day) or more. The specific growth rate on Day 12 to Day 30 after introduction of the Bach2 gene into the B cells is more preferably 0.15 (1/day) or more, and particularly preferably 0.2 (1/day) or more.

The specific growth rate on both of Day 12 to Day 24 and Day 12 to Day 30 after the gene introduction is preferably 0.1 (1/day) or more, more preferably 0.15 (1/day) or more, and further preferably 0.2 (1/day) or more.

Further, the specific growth rate on any one or more of Day 18 to Day 24 and Day 24 to Day 30 after introduction of the Bach2 gene into the B cells is preferably 0.15 (1/day) or more, and more preferably 0.20 (1/day) or more. The specific growth rate on both of Day 18 to Day 24 and Day 24 to Day 30 after the gene introduction is preferably 0.15 (1/day) or more, and more preferably 0.20 (1/day) or more.

It is to be noted that the upper limit of the specific growth rate of the above-mentioned human B cells is not particularly limited, and in general, it is 1.5 (1/day) or less, or 1.0 (1/day) or less.

In the present invention, the term "antigen-specific IgG-positive B cell population," which is used for the cells obtained after the aforementioned selection step, is used to collectively mean the obtained cells, and the meaning of the term is not limited by the number of cells. That is to say, this term is used to indicate a case where there is only a single cell, as well as a plurality of cells.

The antigen-specific IgG-positive B cell population of the present invention is a cell population obtained by the above-described production method. This cell population is mainly composed of IgG-positive B cells having specificity to the used specific antigen, and the IgG-positive B cells having such specificity to the specific antigen have a higher density than, for example, a cell population derived from splenic tissues from a living body primarily contacted with the same antigen as described above. Accordingly, the present antigen-specific IgG-positive B cell population can be preferably used in the production of a monoclonal antibody that requires large quantities of IgG-positive B cells having an affinity for the specific antigen, cell therapy, and the like.

With regard to B cells that constitute the IgG-positive B cell population obtained by the production method of the present invention, a mutation may be introduced into antibody molecules to obtain B cells having a further variety of antigen specificity. An example of such a mutation introduction is introduction of a mutation into a V region. Thereby, the affinity for antigen can be further improved. As a method of introducing a mutation into the V region, a known method can be applied. From the viewpoint of secure mutation introduction, the use of AID (activation induced cytidine deaminase), which contributes to both somatic hypermutation (SHM) to an antibody gene and class switching recombination (CSR) to an antibody constant region gene, is considered. Alternatively, cytokines for reinforcing the expression of AID, and the like may also be used.

As an example of the present invention,
there is provided a method for producing a mouse B cell population, comprising:
a step of culturing mouse B cells on feeder cells presenting CD40L and BAFF on the surface thereof in a medium containing mouse IL-4;
a step of infecting the above-described mouse B cells with a retrovirus vector containing a Bach2 gene; and
a step of culturing the infected mouse B cells in a medium containing mouse IL-21. Moreover, according to the present invention, there is also provided a mouse B cell population produced by the above-described method for producing a mouse B cell population.

As another example of the present invention,
there is provided a method for producing a human B cell population, comprising:
a step of culturing human B cells on feeder cells presenting CD40L and BAFF on the surface thereof in a medium containing human IL-4 and human IL-2;
a step of infecting the above-described human B cells with a retrovirus vector containing a Bach2 gene; and
a step of culturing the infected human B cells in a medium containing human IL-21. Moreover, according to the present invention, there is also provided a human B cell population produced by the above-described method for producing a human B cell population.

The method for producing a monoclonal antibody of the present invention comprises producing a monoclonal antibody, using the cell population obtained by the above described method for producing a B cell population. Thereby, a monoclonal antibody against a specific antigen can be simply and promptly obtained.

In the present method for producing a monoclonal antibody, a publicly known method for producing hybridomas may be applied to the above-described antigen-specific B cell population. Specifically, according to a publicly known cell fusion method, myeloma cells or the like may be applied to the cell population comprising IgG-positive B cells obtained by the present invention, so as to obtain hybridomas. Thereafter, from the obtained hybridomas, hybridomas producing antibodies of interest may be isolated by a limiting dilution method or the like, and antibodies produced from the isolated hybridomas may be then recovered. Alternatively, a method which comprises isolating an antibody gene from the above-described antigen-specific B cell population, and then producing a monoclonal antibody according to genetic recombination, may also be applied.

Hereinafter, the present invention will be described in the following examples. However, these examples are not intended to limit the scope of the present invention. In addition, in the following examples, the symbol "%" is used on a weight (mass) basis.

EXAMPLES

[Example 1] Long-Term Culture of Mouse B Cells (1) Culture of Cells

B cell preparations and other cells were cultured in RPMI-1640 (containing 10% (v/v) FCS, penicillin/streptomycin, 2 mM L-glutamine, 55 nM 2-ME, 10 mM HEPES, and 1 mM sodium pyruvate) that was used as a medium for the culture of B cells, under conditions of 5% (v/v) $CO_2$ and 37° C., unless otherwise specified.

(2) Preparation of Mouse B Cells

Splenic cells were obtained from a mouse (C57BL/6, female, 8-week-old), and were then reacted with a biotin-anti-mouse CD43 antibody (manufactured by BD Pharmingen), a biotin-anti-mouse CD4 antibody (manufactured by Biolegend), a biotin-anti-mouse Ter-119 antibody (manufactured by eBioscience), and a biotin-anti-mouse CD11c antibody (manufactured by eBioscience) according to an ordinary method, so that B cells that were negative to CD43, CD4, Ter-119 and CD11c were recovered using Streptavidin-Particle Plus-DM, BD IMagnet (manufactured by BD Bioscience Pharmingen), thereby obtaining mouse B cells.

(3) Preparation of Retrovirus Vector

Mouse Bcl-6 (Oncogene. 1995 Oct. 19; 11(8): 1657-63), mouse Bach2 (Mol Cell Biol. 1996 November; 16(11): 6083-95), and mouse Bcl-2 (Cell. 1987 May 22; 49(4): 455-63) were each subcloned into the multicloning site of a pMX-IRES-GFP vector (Proc Natl Acad Sci USA, Vol. 97, pp. 3062-3066 (2000)). In addition, a vector into which nothing had been incorporated was used as an empty vector (mock). A retrovirus vector was produced from each of these vectors according to an ordinary method.

(4) Gene Introduction into Mouse B Cells

As 40LB cells that were feeder cells presenting CD40L and BAFF on the surface thereof, the cells described in JP Japanese Patent Publication (Kokai) No. 2011-92142 A were used. The 40LB cells were seeded in a cell density of $3 \times 10^6$ cells on a cell culture plate (manufactured by BD Falcon) having a diameter of 10 cm, and were then cultured for 24 hours, so as to form a single layer. The single layer was then irradiated with γ-ray of 120 Gy, and it was then used as feeder cells. The B cells prepared in (2) above were seeded in a cell density of $1.25 \times 10^4$ cells/ml on the feeder cells, and were then cultured in a B cell culture medium containing mouse IL-4 (10 ng/mL, manufactured by PEPRO TECH). On the third day of the culture, the B cells were infected with each of the retrovirus vectors prepared in (3) above.

On the fifth day of the culture, using PBS containing 2 mM EDTA and 0.5% BSA, the total cells were removed together with the feeder cells from the plate, and were then recovered by flushing with a pipette. The recovered cell population was seeded in a cell density of $2.5 \times 10^3$ cells/ml or less in a B cell culture medium containing mouse IL-21 (10 ng/mL, manufactured by PEPRO TECH) on a newly prepared plate on which 40LB cells had been seeded, and the cell population was then cultured.

The number of B cells of each type seeded on the 5th day of the culture is defined as 1, and the cumulative growth rate of the number of the cells is shown in FIG. 1.

Regarding the B cells of each type, the specific growth rates on Day 5 to Day 9, Day 9 to Day 13, Day 9 to Day 17, Day 9 to Day 22, Day 9 to Day 27, Day 9 to Day 32, and Day 9 to Day 38 are shown in FIG. 2.

Also, regarding the B cells of each type, the specific growth rates on Day 5 to Day 9, Day 9 to Day 13, Day 13 to Day 17, Day 17 to Day 22, Day 22 to Day 27, Day 27 to Day 32, and Day 32 to Day 33 are shown in FIG. 3.

The longitudinal axis in the graphs shown in FIG. 2 and FIG. 3 indicates the unit of the specific growth rate that is (1/day).

As shown in FIG. 1, in the case of B cells transformed by mock or Bcl2, the cells hardly proliferated after Day 9. In addition, the specific growth rate (1/day) of B cells transformed by Bcl6 was approximately 0.2, whereas B cells transformed by Bach2 maintained a specific growth rate of 0.4 or more even on Days 32 to 38.

[Example 2] Long-Term Culture of Human B Cells (1) Preparation of Retrovirus Vector A hCD8 fragment was prepared from pMX-IRES-hCD8 (Nat Commun. 2011 Sep. 6; 2: 465) by digesting with NcoI-SalI, and it was then subcloned into the NcoI-SalI site of a pMXs-IG vector (EMBO J. 1999 Sep. 1; 18(17): 4754-65), so as to prepare pMXs-IRES-hCD8. This was used as an empty vector (mock). Human Bach2 (Oncogene. 2000 Aug. 3; 19(33): 3739-49) was subcloned into the BamHI-NotI site of pMXs-IRES-hCD8, such that it comprised a Kozak sequence, so as to prepare pMXs-hBach2-IRES-hCD8. This was used as a human Bach2 expression vector. A retrovirus vector was produced from each of these vectors according to an ordinary method.

(2) Preparation of Human B Cells

Lymphocytes were separated from the peripheral blood of a healthy human subject, using Ficoll-Paque PLUS (manufactured by GE Healthcare). Thereafter, the lymphocytes were reacted with a biotin-anti-human CD2 antibody (manufactured by Biolegend) and a biotin-anti-human CD235a antibody (manufactured by eBioscience) according to an ordinary method. Then, CD2- and CD235-negative cells were recovered using Streptavidin-Particle Plus-DM, BD IMagnet (manufactured by BD Bioscience Pharmingen). The recovered cells were reacted with a PE/Cy7 anti-human CD19 antibody according to an ordinary method, and CD19-positive cells were then sorted out using ARIAII (manufactured by BD Biosciences), so as to obtain human B cells.

(3) Gene Introduction into Human B Cells

The recovered B cells were cultured in a B cell culture medium containing human IL-4 (50 ng/mL, manufactured by PEPRO TECH) and human IL-2 (25 unit/ml, manufactured by PEPRO TECH) on 40LB prepared in the same manner as that of Example 1. On the fourth day of the culture, the B cells were infected with each of the retrovirus vectors prepared in (1) above. On the sixth day of the culture, using PBS containing 2 mM EDTA and 0.5% BSA, the total cells were removed together with the feeder cells from the plate, and were then recovered by flushing with a pipette. The recovered cell population was seeded in a cell density of $1 \times 10^5$ cells/ml or less in a B cell culture medium containing human IL-21 (10 ng/mL, manufactured by PEPRO TECH) on a newly prepared plate on which 40LB cells had been seeded, and the cell population was then cultured.

The number of B cells of each type seeded on the 6th day of the culture is defined as 1, and the cumulative growth rate of the number of the cells is shown in FIG. 4.

Regarding the B cells of each type, the specific growth rates on Day 6 to Day 12, Day 12 to Day 18, Day 12 to Day 24, and Day 12 to Day 30 are shown in FIG. 5.

Also, regarding the B cells of each type, the specific growth rates on Day 6 to Day 12, Day 12 to Day 18, Day 18 to Day 24, and Day 24 to Day 30 are shown in FIG. 6.

The longitudinal axis in the graphs shown in FIG. 5 and FIG. 6 indicates the unit of the specific growth rate, (1/day).

Human B cells can be cultured for a long period of time by the above-described method.

[Example 3] Long-Term Culture of Human B Cells Using Lentivirus Vector (1) Preparation of Lentivirus Vector Human Bach2 (Oncogene. 2000 Aug. 3; 19(33): 3739-49) was subcloned into the multicloning site of CS2-/CMV-MCS (Virology. 2009 Oct. 25; 393(2): 198-209). A lentivirus vector was prepared according to the method described in Virology. 2009 Oct. 25; 393(2): 198-209. A vector into which human Bach2 had not been subcloned was used as an empty vector (mock).

(2) Preparation of Human B Cells

Monocytes were separated from the peripheral blood of a healthy human subject, using Lymphoprep Tube (manufactured by Axis-Shield PoC AS), and human B cells were then obtained from the monocytes, using B Cell Isolation Kit II, human (manufactured by Miltenyi Biotec).

(3) Gene Introduction into Human B Cells

The recovered B cells were infected with each of the retrovirus vectors prepared in (1) above. After completion of the infection, the cells were seeded in a cell density of $1.25 \times 10^4$ cells/ml on a cell culture plate (manufactured by BD Falcon) having a diameter of 10 cm, and were then cultured in a B cell culture medium containing an anti-CD40 antibody (1 µg/ml, manufactured by Beckman Coulter), secretory human BAFF (1 µg/ml, manufactured by PEPRO TECH), human IL-4 (50 ng/mL, manufactured by PEPRO TECH), and human IL-2 (25 unit/ml, manufactured by PEPRO TECH). On the fifth day of the culture, the total cells were recovered, and were then cultured in a B cell culture medium containing an anti-CD40 antibody (1 µg/ml, manufactured by Beckman Coulter), secretory human BAFF (1 µg/ml, manufactured by PEPRO TECH), human IL-21 (10 ng/mL, manufactured by PEPRO TECH), and human IL-2 (25 unit/ml, manufactured by PEPRO TECH).

Human B cells can be cultured for a long period of time by the above-described method.

---

The invention claimed is:

1. A method for producing a monoclonal antibody, wherein a B cell population produced by a method comprising culturing B cells, in which the expression of a Bach2 gene has been increased, in the presence of a means for acting on CD40 and/or a BAFF receptor.

* * * * *